(12) United States Patent
Haidukewych

(10) Patent No.: US 9,005,304 B2
(45) Date of Patent: Apr. 14, 2015

(54) ACETABULAR PROSTHETIC DEVICE

(71) Applicant: George J. Haidukewych, Orlando, FL (US)

(72) Inventor: George J. Haidukewych, Orlando, FL (US)

(*) Notice: Subject to any disclaimer, the term of this patent is extended or adjusted under 35 U.S.C. 154(b) by 117 days.

(21) Appl. No.: 13/987,624

(22) Filed: Aug. 15, 2013

(65) Prior Publication Data

US 2013/0338786 A1    Dec. 19, 2013

Related U.S. Application Data

(63) Continuation-in-part of application No. 13/374,841, filed on Jan. 18, 2012, now Pat. No. 8,556,986.

(51) Int. Cl.
*A61F 2/32* (2006.01)
*A61F 2/34* (2006.01)
*A61F 2/30* (2006.01)

(52) U.S. Cl.
CPC ......... *A61F 2/34* (2013.01); *A61F 2002/30428* (2013.01); *A61F 2002/30387* (2013.01); *A61F 2002/30433* (2013.01); *A61F 2002/30578* (2013.01); *A61F 2002/30736* (2013.01)

(58) Field of Classification Search
CPC ............ A61F 2/34; A61F 2002/30387; A61F 2002/30578; A61F 2002/30428
USPC ........................................ 623/22.11, 22.39
See application file for complete search history.

(56) References Cited

U.S. PATENT DOCUMENTS

2013/0035766 A1* 2/2013 Meridew ................... 623/22.21

* cited by examiner

*Primary Examiner* — Jason-Dennis Stewart
(74) *Attorney, Agent, or Firm* — Arthur W. Fisher, III

(57) ABSTRACT

An acetabular prosthetic device comprising at least one acetabular augment coupled to an acetabular cup by an augment coupling element to secure the acetabular prosthetic device in place wherein the acetabular cup comprises a shell having at least one groove formed on the outer surface thereof to slidably receive the augment coupling element therein and the acetabular augment comprises an augment body configured to engage the shell and the ilia bone such that the augment coupling element is moved along the groove to position the acetabular body to engage both the shell and ilia bone to secure the acetabular prosthetic device in place.

5 Claims, 14 Drawing Sheets

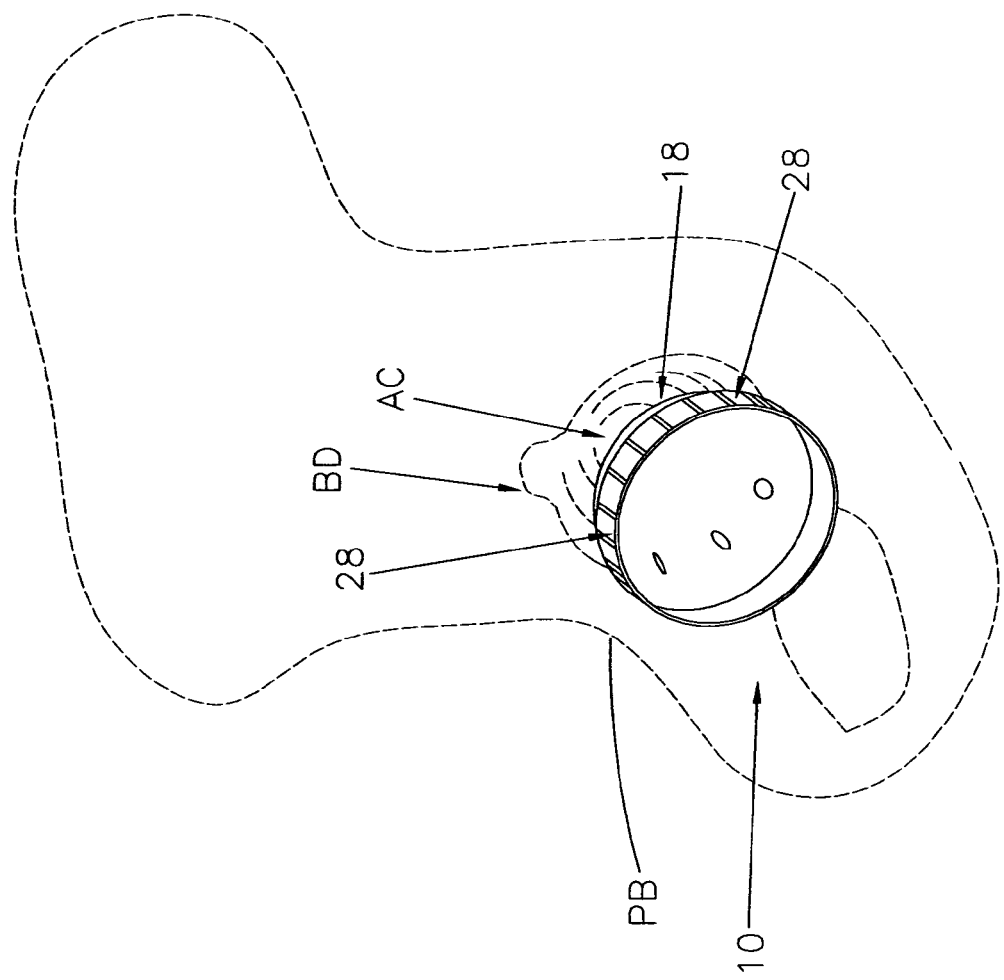

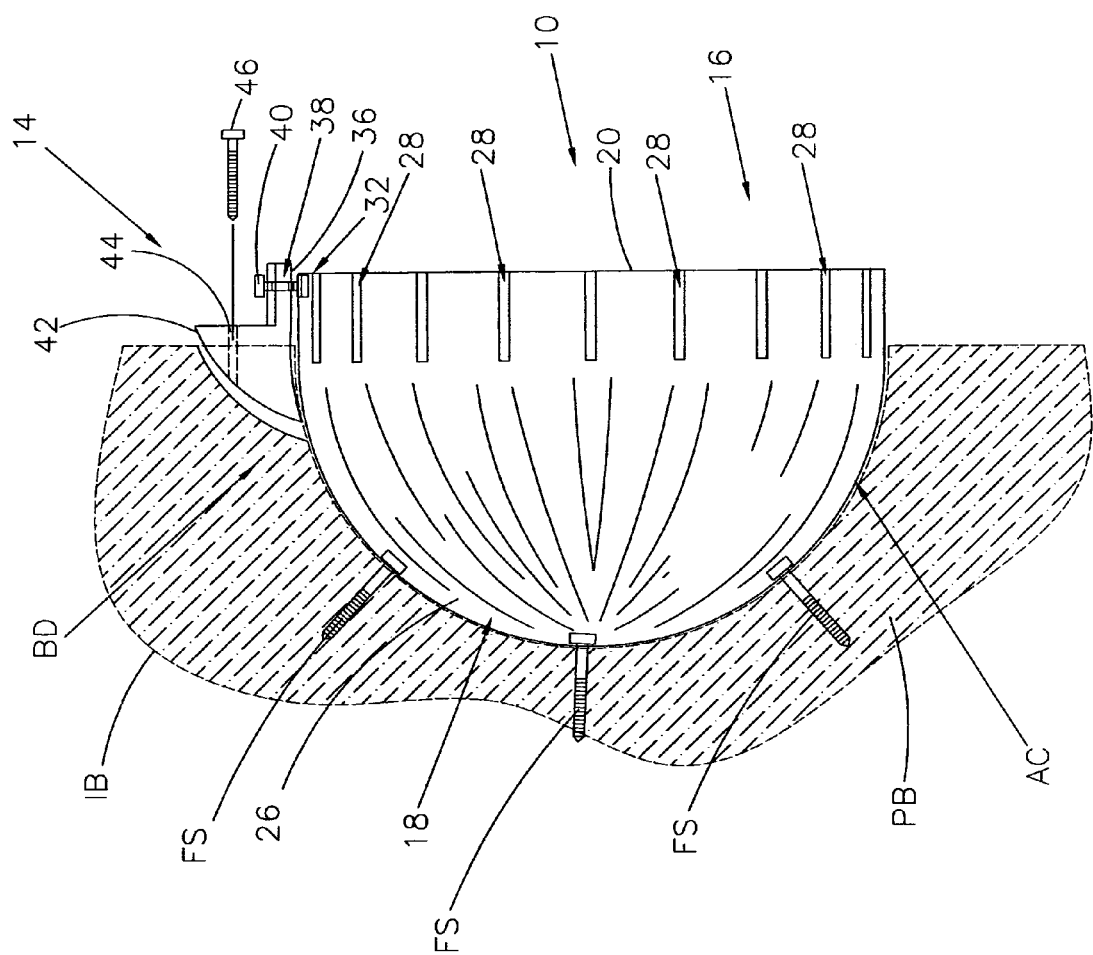

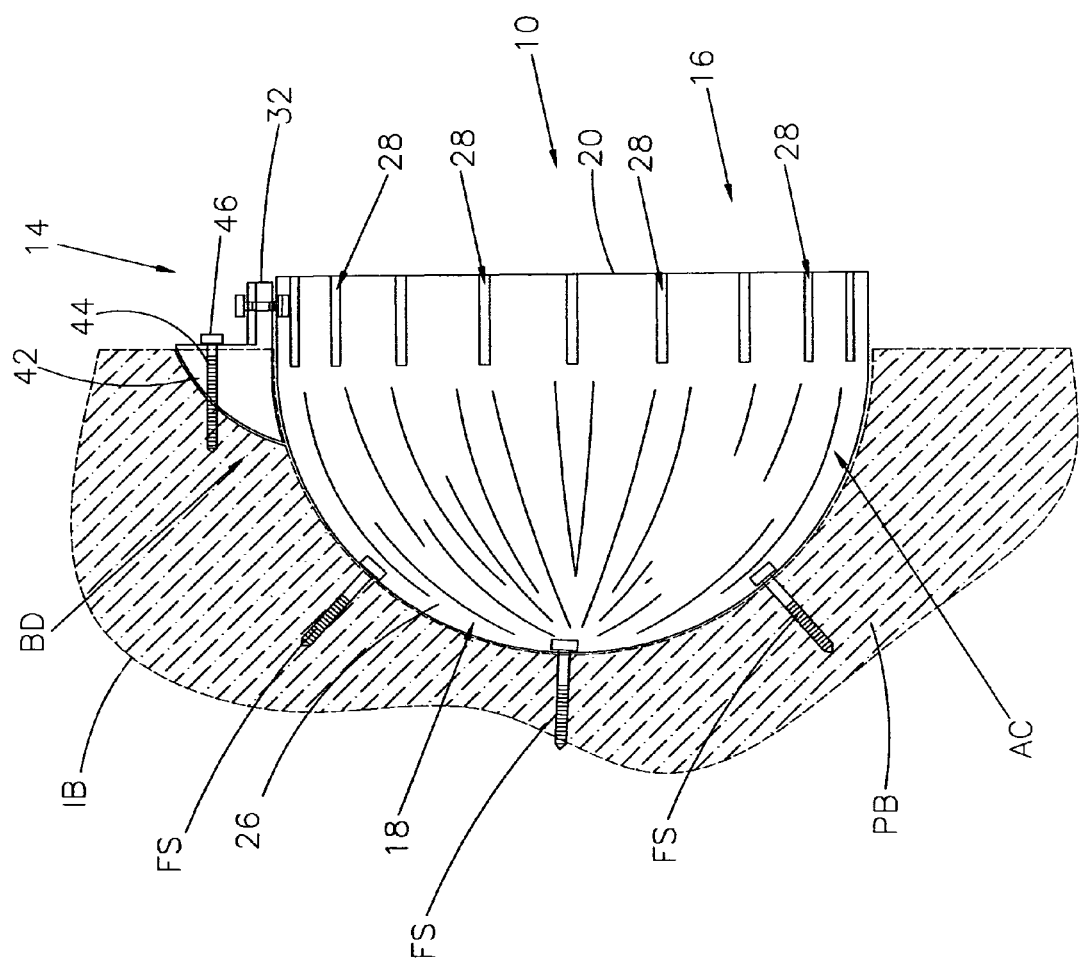

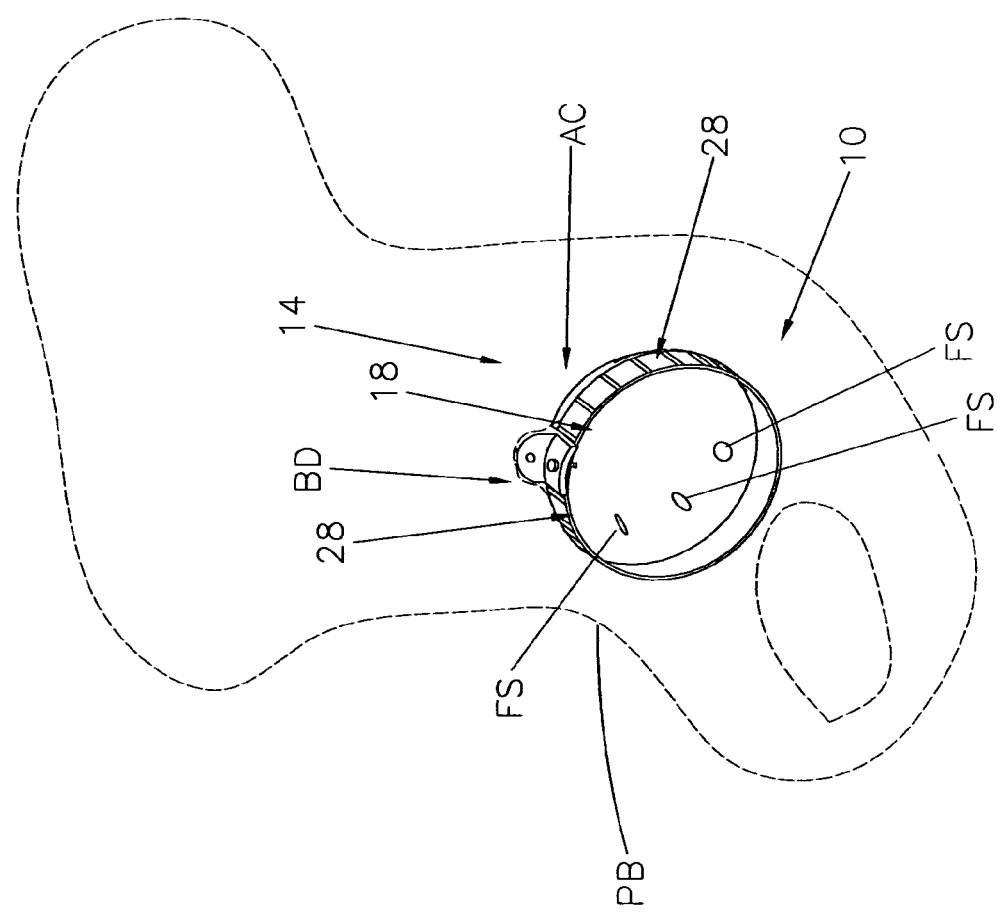

1

ACETABULAR PROSTHETIC DEVICE

CROSS REFERENCE

This is a continuation of co-pending application Ser. No. 13/374,841 filed Jan. 18, 2012.

BACKGROUND OF THE INVENTION

1. Field of the Invention

An acetabular prosthetic device for use with a prosthetic hip implant comprising at least one acetabular augment coupled to an acetabular cup to secure the acetabular prosthetic device in place.

2. Description of the Prior Art

US Pat. No. 2005/0171614 ('614) relates to an acetabular implant comprising an expandable acetabular cup including an internal cavity to receive a conical core to radially expand the acetabular cup. The acetabular cup is cut into sectors by slots 30 to facilitate the radial expansion of the acetabular cup upon insertion of the conical core. In addition, holes and ribs contribute to increasing the flexibility of each segment of the acetabular cup to facilitate the expansion of the acetabular cup.

The acetabular cup is anchored to the bone cavity by the radial expansion of the acetabular cup by insertion of the conical core with the internal cavity of the acetabular cup (page 2, paragraph [00327]). Moreover, the circumferential rib on the extension of the flat bottom about the central hole is intended to improve or enhance the anchoring of the acetabular cup to the acetabular (page 3, paragraph [0035]).

In short, '614 teaches the use of slots and holes for the sole purpose of allowing the acetabular cup to expand to "fit" the particular bone structure of the patient. Significantly, there is no acetabular augment, in any form or manner, contrary to Applicant's invention.

US Pat. No. 2013/0035766 ('766) describes a pelvic implant comprising a patient-specific flange including a generic first surface and a patient-specific second surface designed and machined to nest in the particular patient's peracetabular anatomy (page 3, paragraph [00337].

The patient-specific second surface is preoperatively configured from a three-dimensional digital image of the pelvis under the flange in given or selected location or position on the acetabular. Specific reference has been made to FIG. 10 where the entire flange is preoperatively designed to the specific patient's peracetabular anatomy to preclude the need of intraoperative bending or other deformation by the surgeon. In this respect, the patient-specific flange is designed with adequate thickness for stability and rigidity without using any spacers or adjustable fasteners. In other words, the width or thickness "t" of each flange is designed and fabricated to the particular three dimensional digital image of the pelvic of an individual patient to mate and closely conform to the negative or obverse of the corresponding surface of the pelvis under the flange (page 1, paragraph [00037]).

The patient-specific flange is removably connected to the acetabular cup. The patient-specific flange is shown to have a connecting portion with an opening for receiving a fastener from a corresponding connecting portion of the acetabular cup. General reference is made to other types of modular connectors; i.e. such as tongue-and-groove.

'766 also discloses an ischial blade and an obturator foramen hook coupled in addition to the bifurcated lilac flange removably coupled to the acetabular cup by snap-fit and/or fasteners. Note worthy is that fasteners may or may not be used. The ischial blade and obturator foramen hook are not retained in the channels or slots. The width of these elements and are less the width of the corresponding channel or slot. The lower portions of elements and are snapped or press-fitted into pockets or slots at the lower end of the corresponding channel. There is no adjustable structure to accommodate the variations in the particular bone structure. The elements may be bent to assist in stabilizing the acetabular cup.

Significantly, there is no description or depiction to suggest any departure from the teaching of '766. The thickness of the patient-specific flange is custom fabricated for each individual patient to account for anatomical variations. There is no structure capable of providing a universal feature to provide for a single acetabular implant device for general use.

The teachings of US 2005/0171614 (expandable acetabular cup without an acetabular augment) and '766 (acetabular augment flange individually fabricated to thickness and configuration dictated by the patient's particular pelvis anatomical shape) are so disparate that there is no motivation or suggestion to combine either the structures or functions of these two references to render Applicant's invention obvious.

The passing reference to a tongue-and-groove connector (not shown) to replace the connection portion of the acetabular cup and the fixed fastener does not teach or suggest the structure or function capable of movement of the acetabular augment relative to the acetabular cup to account for variations of in different patient's pelvic anatomy. The essence of '766 is the shim-like configuration of flange. Moreover, the disposition of the connecting portion would not allow for the use (installation) of an acetabular coupling element.

The mating structure of the augment coupling element and the groove within the shell of Applicant's acetabular prosthetic device permits the relative movement of the augment coupling element within the groove to provide the universal use of the acetabular prosthetic with varying anatomical sites without the necessity of patient-specific customization to anchor the acetabular cup in place.

U.S. Pat. No. 5,176,711 shows an implantable acetabular hip prosthesis including a primary shell having an outer surface to be received within a surgically prepared acetabulum and an inner cavity for receiving a bearing insert which, in turn, receives a femoral head portion of a femoral component of a total hip prosthesis. The acetabular component of the prosthesis further includes an augmentation piece to be attached to the primary shell fixedly retained in a selected one of a plurality of angular orientations relative to the primary shell.

U.S. Pat. No. 6,454,809 describes a acetabular or cotyloid implant having at least one dove-tail groove found on an outer surface thereof to receive an augmentation element.

U.S. Pat. No. 7,985,260 and US 2011/0264232 show an acetabular prosthesis system coupled to a surgically-prepared acetabulum includes an acetabular shell, an augment component and a fastener to couple the acetabular shell and the augment component together.

U.S. Pat. No. 7,993,408 teaches an orthopedic prosthesis for implantation comprising a shell, an augment and a securing member. An elongated slot extends between the outer and inner surfaces of the shell. The augment defines a body having a passage therethrough. The securing member extends through the passage and the slot. The securing member is movable between a locked position wherein the augment is precluded from relative movement with the shell and an unlocked position wherein the securing member is adapted to slidably traverse along the slot to locate the augment at a plurality of positions relative to the shell.

US 2008/0021568 relates to a prosthetic acetabular cup having an augment attached to an acetabular cup by a coupling element including an outer dovetail portion which slidably engages a groove formed within the augment. The inner end of the coupling element engages screw holes on the acetabular cup. The groove of the augment further includes a second end having a gradually increasing distance from the outer surface of the shell and the inner surface of the augment on moving towards the second end of the augment.

Additional examples are found in the following prior art: U.S. Pat. Nos. 7,595,715, 7,947,083, US 2007/0173948 and US 2010/00044754

While some of the prior art may contain some similarities relating to the present invention, none of them teach, suggest or include all of the advantages and unique features of the invention disclosed hereafter.

SUMMARY OF THE INVENTION

The present invention relates to an acetabular prosthetic device for use with a prosthetic hip implant comprising at least one acetabular augment coupled to an acetabular cup by an augment coupling element to secure the acetabular prosthetic device to the ilia bone.

The acetabular cup comprises a shell to rotatably receive a substantially spherical portion of the prosthetic hip implant therein having at least one groove formed therein to slidably receive the augment coupling element.

The acetabluar augment comprises an augment body to engage the outer surface of the shell having at least one coupling aperture to receive a corresponding fastener or screw therethrough to operatively engage the augment coupling element to secure the acetabular augment to the acetabular cup when the acetabular prosthetic device is surgically positioned in the patient and a bone engaging surface to engage the ilia bone having at least one acetabular aperture to receive a corresponding fastener or screw therethrough to secure the augment body to the ilia bone when the acetabular augment and the acetabular cup are surgically positioned in the patient.

The augment coupling element comprises an enlarged inner member and an internally threaded reduced outer member. The groove formed in the shell comprises a conversely shaped configuration to the augment coupling element, i.e., an enlarged inner or interior space configured to receive the enlarged inner member of the augment coupling element and a reduced outer slot to receive the internally threaded reduced outer member of the acetabular coupling element such that when a fastener or screw is passed through the augment body of the acetabular augment and threaded into the internally threaded reduced outer member the surface of the enlarged inner member and the surface of the distal enlarged space are pressed together to secure the acetabular augment in place along the groove.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which: Similar reference characters refer to similar parts throughout the several views of the drawings.

FIG. 9A is a perspective view of the acetabular cup of the present invention

FIG. 10 is a side view of the acetabular cup of the present invention impacted and stabilized in the acetabulum cavity having at least a portion of the augment coupling element positioned in the groove of the acetabular cup after the acetabular augment and augment coupling element are assembled together.

FIG. 12 is a side view of the acetabular cup of the present invention impacted and stabilized in the acetabulum cavity with the acetabular augment anchored to the lateral ilia bone and secured to the acetabular cup by the augment coupling element.

FIG. 12A is a perspective view of the acetabular cup of the present invention impacted and stabilized in the acetabulum cavity with the acetabular augment anchored to the lateral ilia bone and secured to the acetabular cup by the augment coupling element.

Similar reference characters refer to similar parts throughout the several views of the drawings.

DETAILED DESCRIPTION OF THE INVENTION

Figure 1:
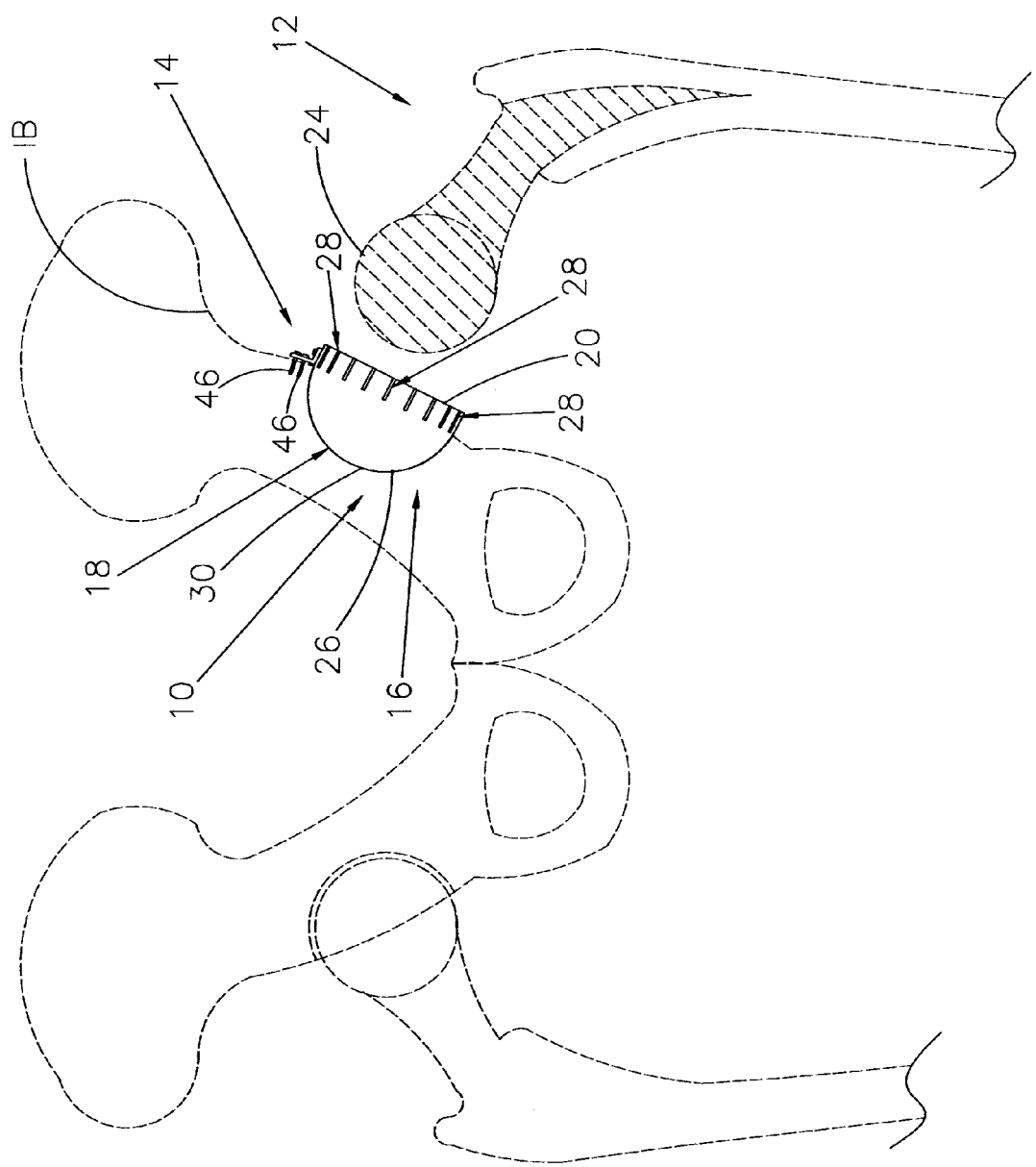
FIG. 1 is a side view of the acetabular prosthetic device of the present invention.
Figure 2:
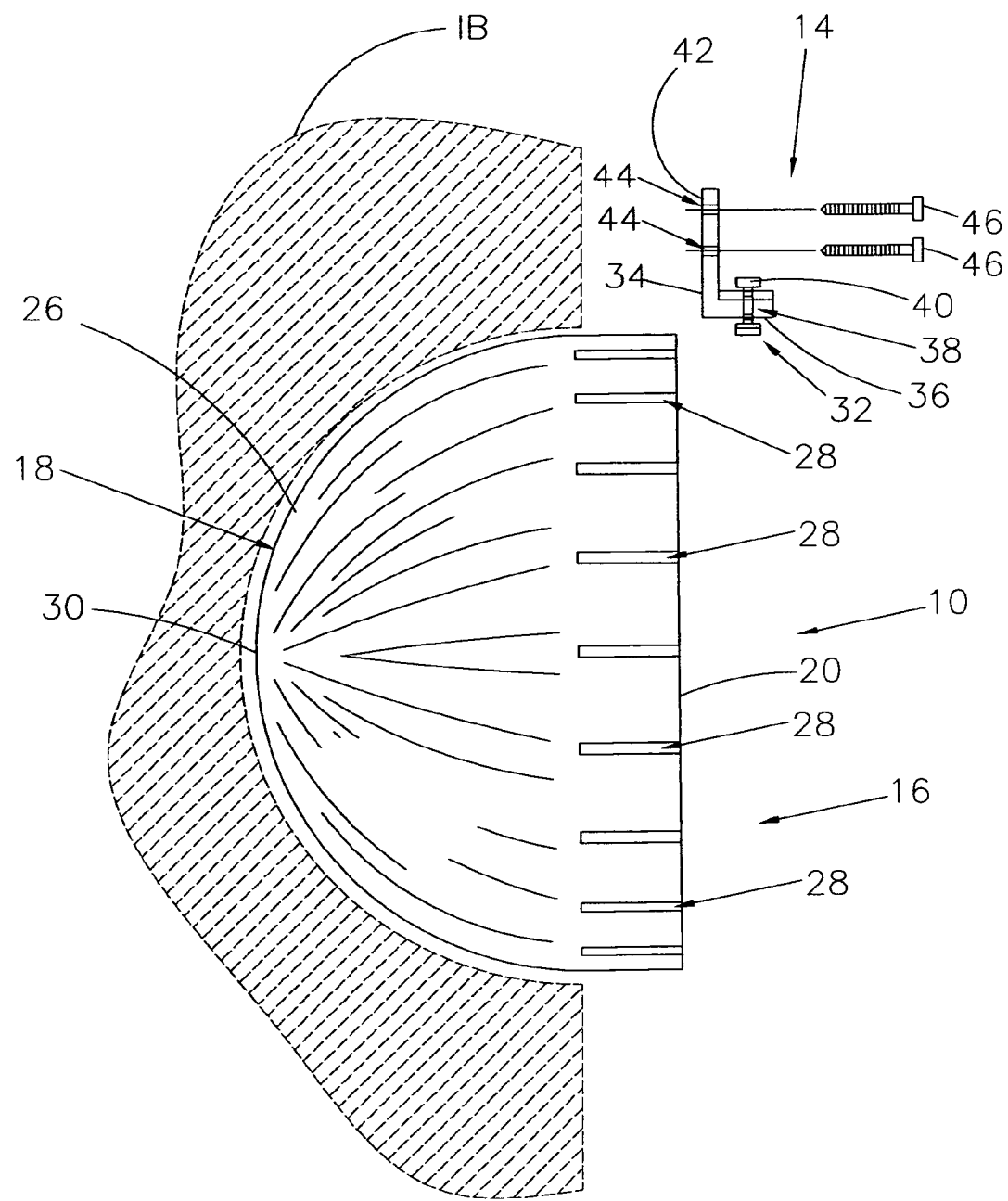
FIG. 2 is an exploded side view of the acetabular prosthetic device of the present invention.
Figure 3:
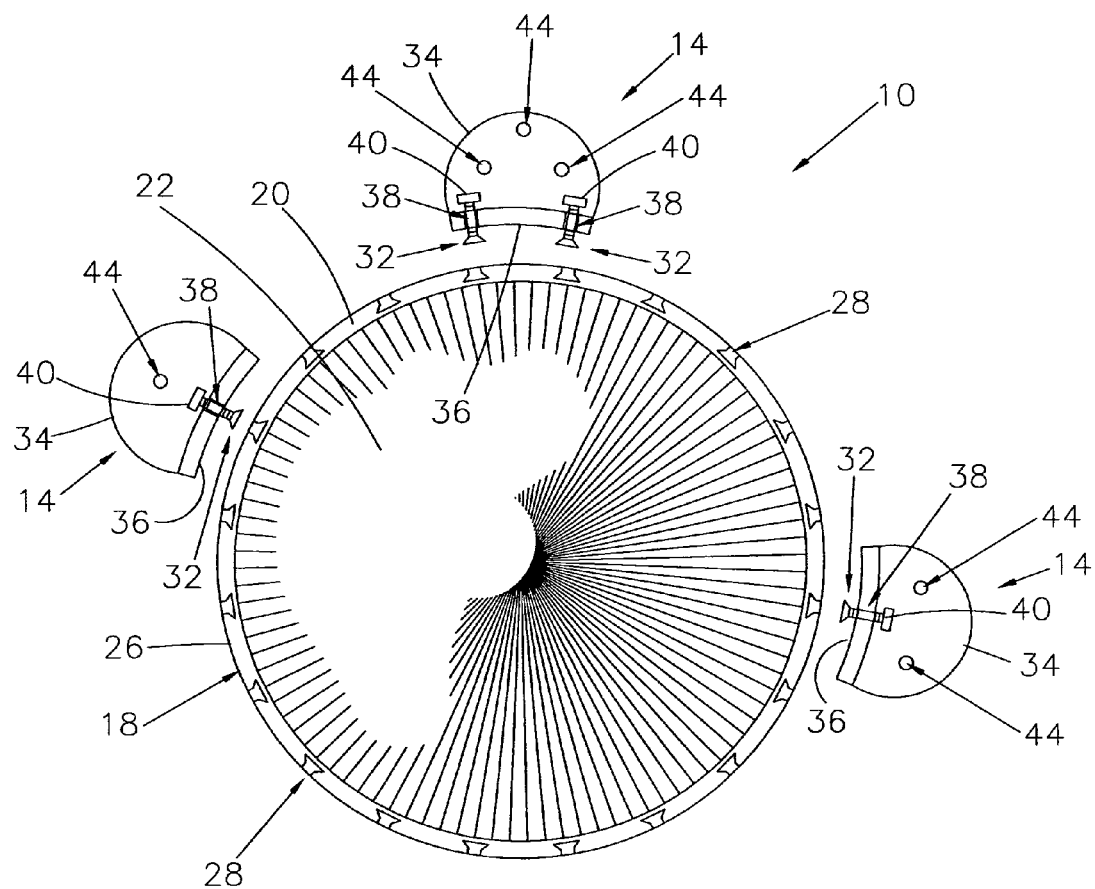
FIG. 3 is an exploded bottom view of the acetabular prosthetic device of the present invention.
Figure 4:
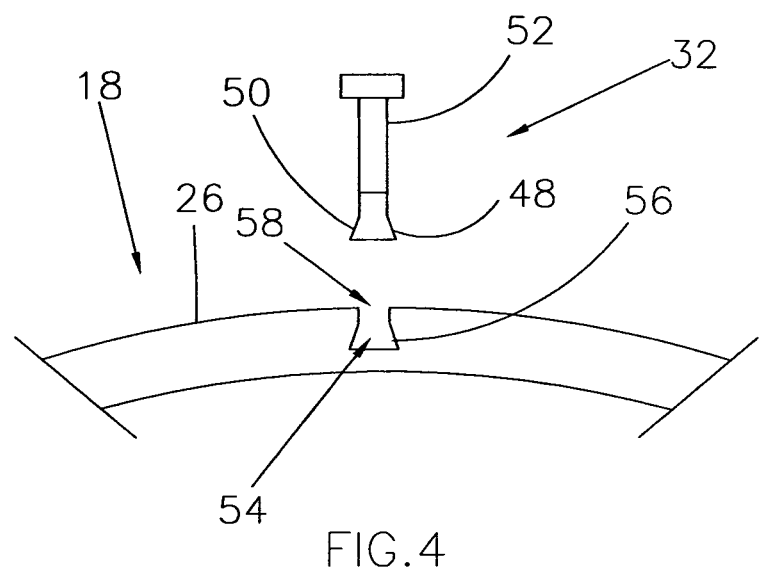
FIG. 4 is a side view of the augment coupling element of the present invention.
Figure 5:
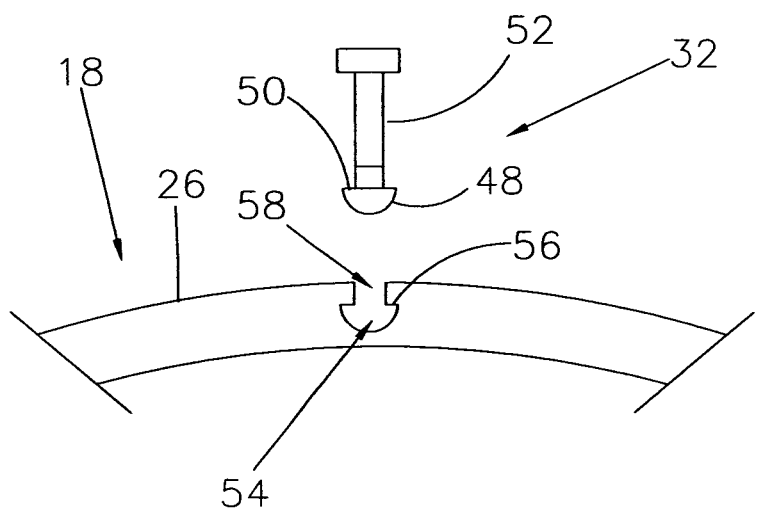
FIG. 5 is a side view of an alternate embodiment of the augment coupling element of the present invention.
Figure 6:
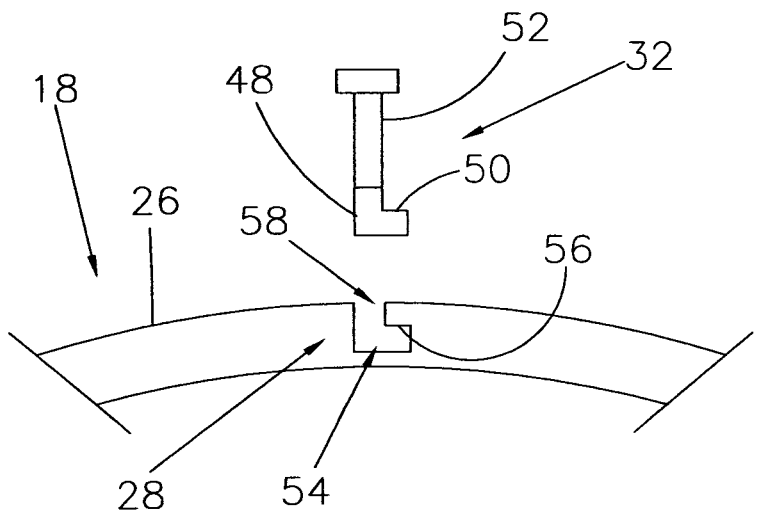
FIG. 6 is a side view of another alternate embodiment of the augment coupling element of the present invention.
Figure 7:
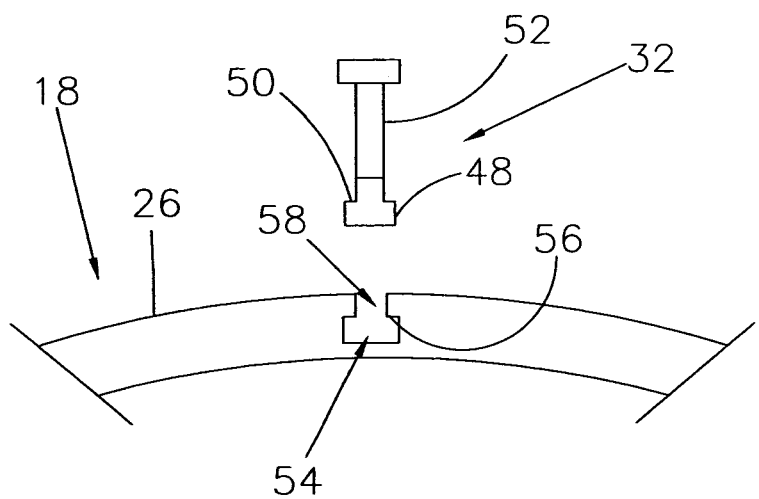
FIG. 7 is a side view of yet another alternate embodiment of the augment coupling element of the present invention.

As shown in FIGS. 1 through 3, the present invention relates to an acetabular prosthetic device generally indicated as 10 for use with a prosthetic hip implant generally indicated as 12 comprising at least one acetabular augment generally indicated as 14 coupled to an acetabular cup generally indicated as 16 to secure the acetabular prosthetic device 10 in place on the ilia bone (IB).

The acetabular cup 16 comprises a shell generally indicated as 18 including a substantially circular base 20 having an inner substantially concave surface 22 to rotatably receive a substantially spherical portion 24 of the prosthetic hip implant 12 therein and an outer substantially convex surface 26 having at least one groove 28 formed therein extending from the substantially circular base 20 of the shell 18 of the acetabular cup 16 toward the apex 30 thereof to slidably receive an augment coupling element generally indicated as 32.

The acetabluar augment 14 comprises an augment body 34 including a substantially concave surface 36 to engage the outer substantially convex surface 26 of the shell 18 of the acetabular cup 16 having at least one coupling aperture or recess 38 to receive a corresponding fastener or screw 40 therethrough to operatively engage the augment coupling element 32 to secure the augment body 34 of the acetabular augment 14 to the shell 18 of the acetabular cup 16 when the acetabular prosthetic device 10 is surgically positioned in the patient and a bone engaging surface 42 to engage the ilia bone IB having at least one acetabular aperture or recess 44 to receive a corresponding fastener or screw 46 therethrough to secure the augment body 34 of the acetabular augment 14 to the ilia bone IB when the acetabular augment 14 and the acetabular cup 16 are surgically positioned in the patient. As best shown in FIG. 2, the center-line(s) of fastener(s) or screw(s) 40 is substantially perpendicular to the center-line(s) of fastener(s) or screw(s) 46.

FIGS. 4 through 7 show several embodiments of the augment coupling element 32. Specifically, each augment coupling element 32 comprises a distal enlarged inner member 48 including a proximal surface 50 and a proximal internally threaded reduced outer member 52 to receive the corresponding fastener or screw 40. The groove 28 formed in the shell 18 of the acetabular cup 18 comprises a converse configuration to the corresponding augment coupling element 32, i.e., a distal enlarged inner or interior space 54 including a proximal surface 56 configured to receive the correspondingly shaped distal enlarged inner member 48 of the augment coupling element 32 such that the proximal surface 50 of the distal enlarged inner member 48 engages the proximal surface 56 of the distal enlarged inner or interior space 54 and a reduced outer slot 58 to receive the proximal internally threaded reduced outer member 52 of the corresponding acetabular coupling element 32. When a fastener(s) or screw(s) 40 is passed through the coupling aperture(s) or recess(es) 38 formed in the augment body 34 of the acetabular augment 14 and threaded into the proximal internally threaded reduced outer member 52, the proximal surface 50 of the distal enlarged inner member 48 and the proximal surface 56 of the distal enlarged inner or interior space 54 are pressed together to secure the acetabular augment 14 in place operatively positioned along the groove 28 with the bone engaging surface 48 secured to the ilia bone IB by a fastener(s) or screw(s).

In particular, FIGS. 4 through 7 depict the distal enlarged inner end portion 48 as a frustum conical or truncated triangular in cross-section configuration, a hemispherical configuration, an L-shaped configuration and a T-shaped configuration respectively with the corresponding groove 28 having a converse configuration, in addition to the acetabular cup 16.

Of course, the shell 18 of the acetabular cup 16 maybe glued or otherwise fastened or secured in typical fashion, surgical procedure.

FIGS. 8 through 12A are helpful in understanding several methods of implanting the acetabular cup 16 and the acetabular augment 14 in the pelvic bone PB.

Figure 8:
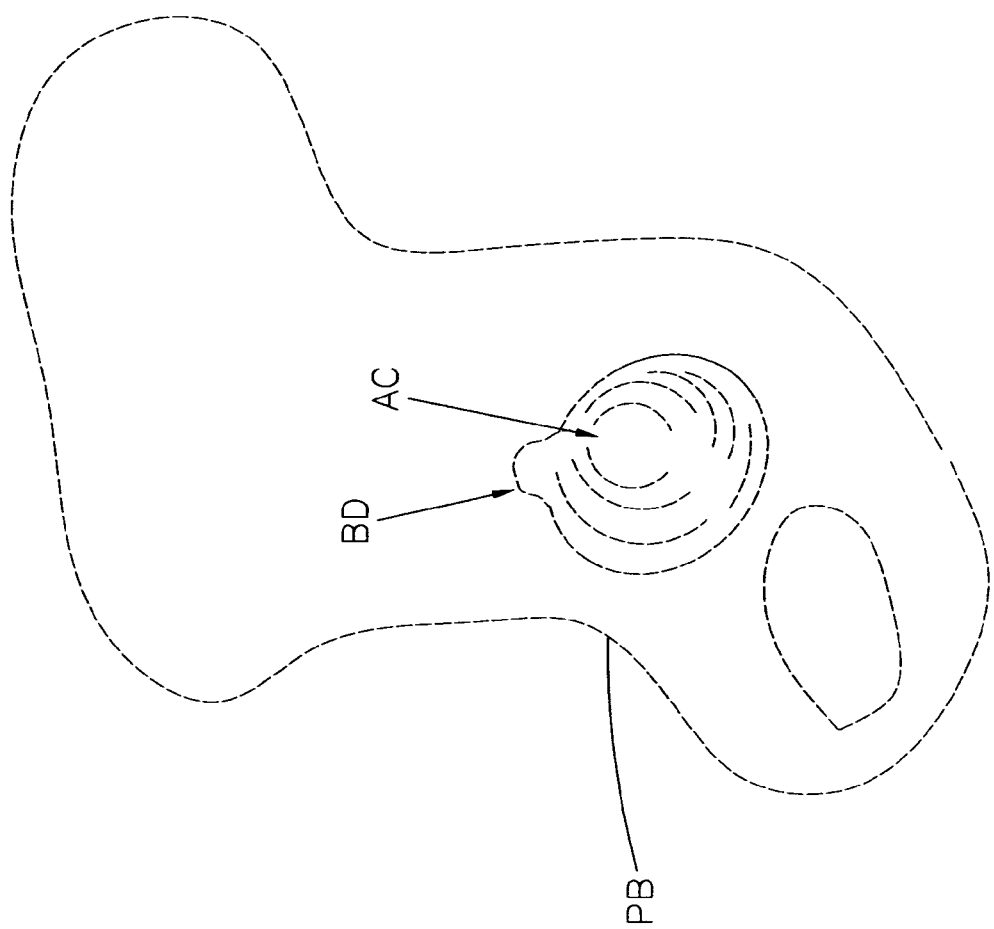
FIG. 8 depicts the acetabulum cavity of the pelvic bone with a bony deficiency.
Figure 9:
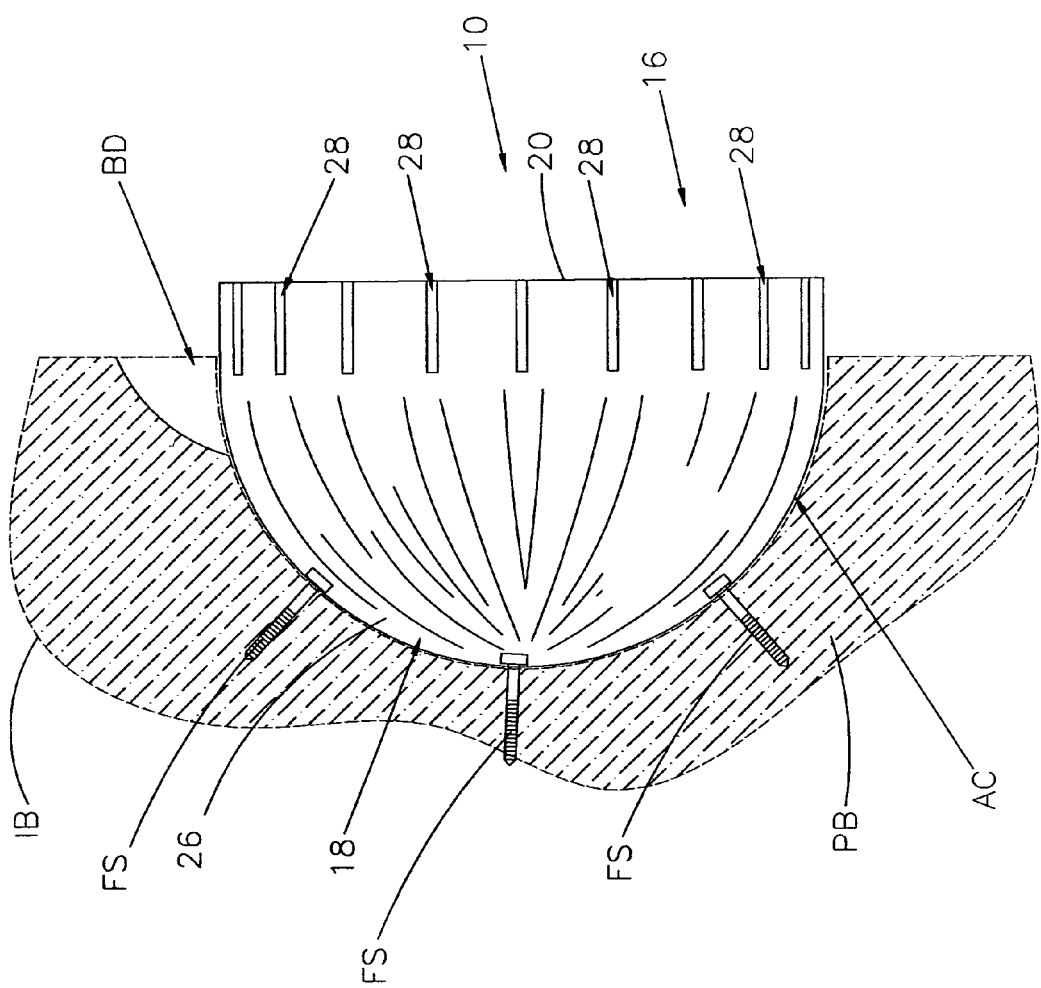
FIG. 9 is a side view of the acetabular cup of the present invention impacted and stabilized in the acetabulum cavity.
Figure 10A:
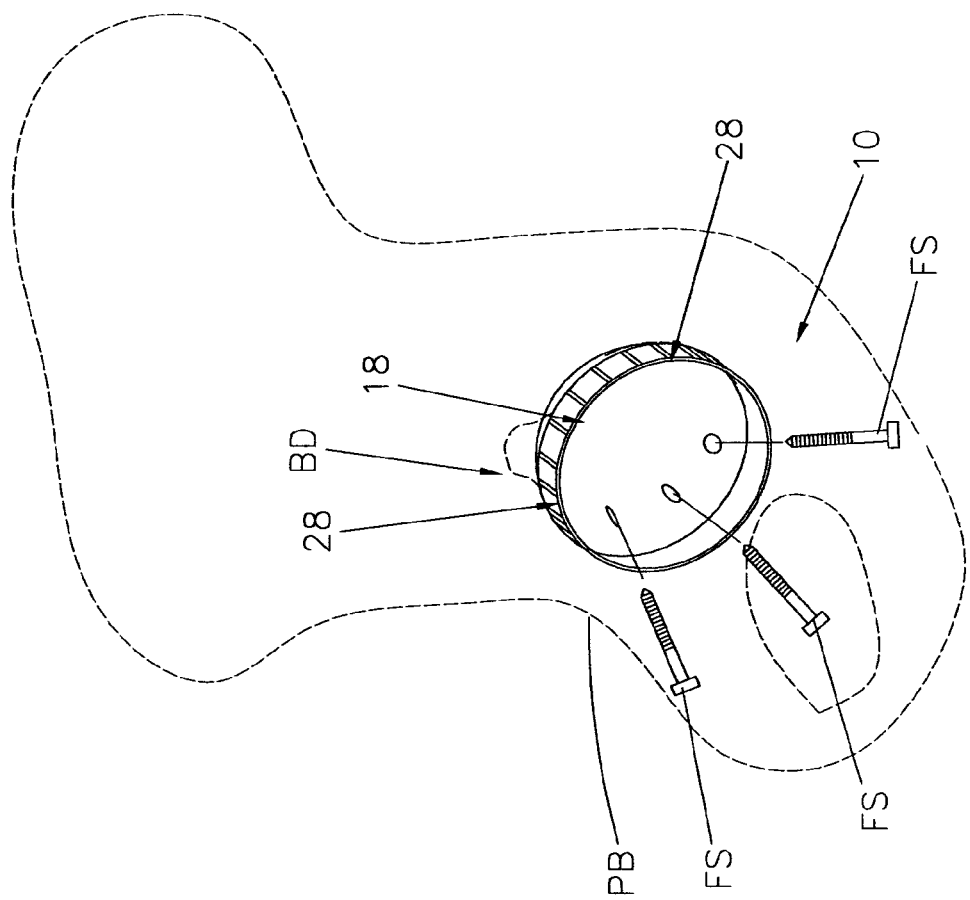
FIG. 10A is a perspective view of the acetabular cup of the present invention impacted in the acetabulum cavity.

FIG. 8 illustrates the acetabulum cavity AC and a bony deficiency (BD) in the pelvic bone PB.

Initially, the acetabulum cavity AC is prepared to receive the acetabular cup 16 by reaming the acetabulum site. The acetabular cup 16 is then placed or positioned in the acetabular cavity AC in the preferred orientation for best bone contact and hip stabilization. The acetabular cup 16 is then impacted into the acetabulum cavity AC and stabilized or secured in place by at least one screw FS or similar fastener as shown in FIGS. 9, 9A, 10A and 11A.

Figure 11:
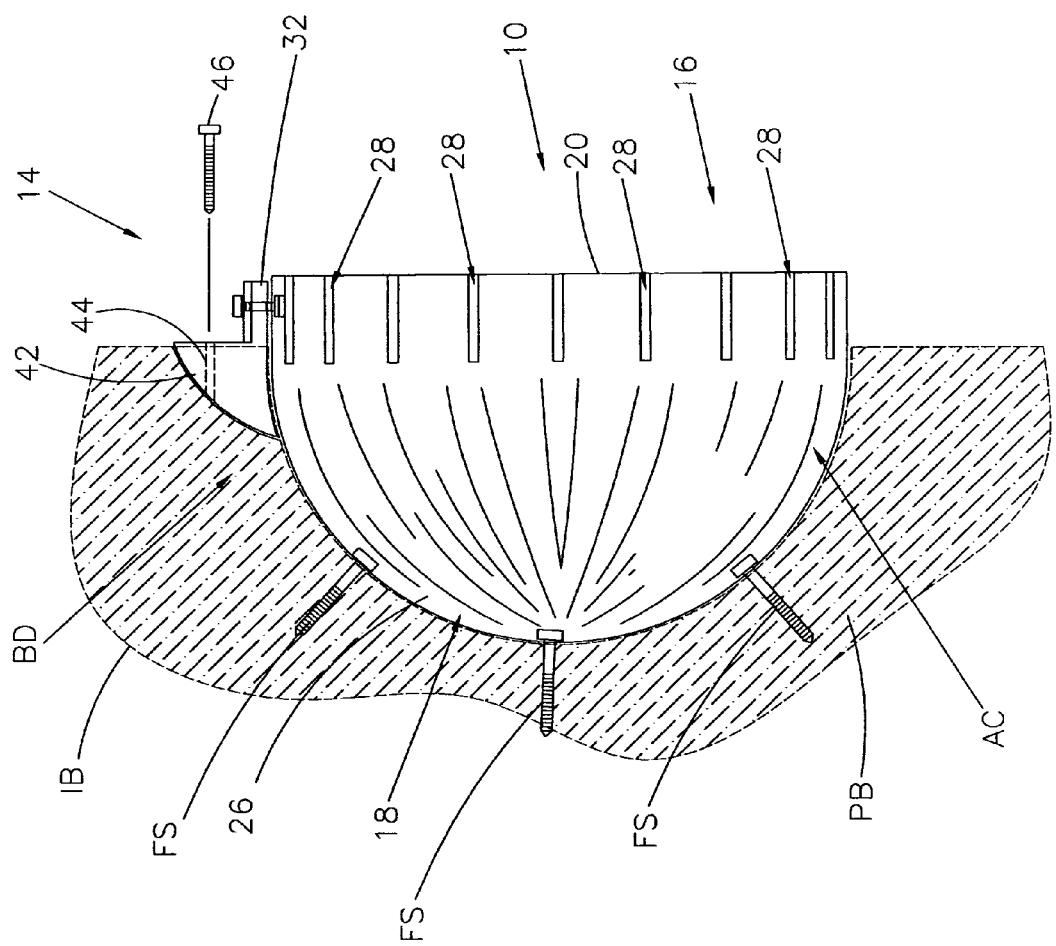
FIG. 11 is a side view of the acetabular cup of the present invention impacted and stabilized in the acetabulum cavity with the acetabular augment engaging the lateral ilia bone and the outer surface of the acetabular cup.
Figure 11A:
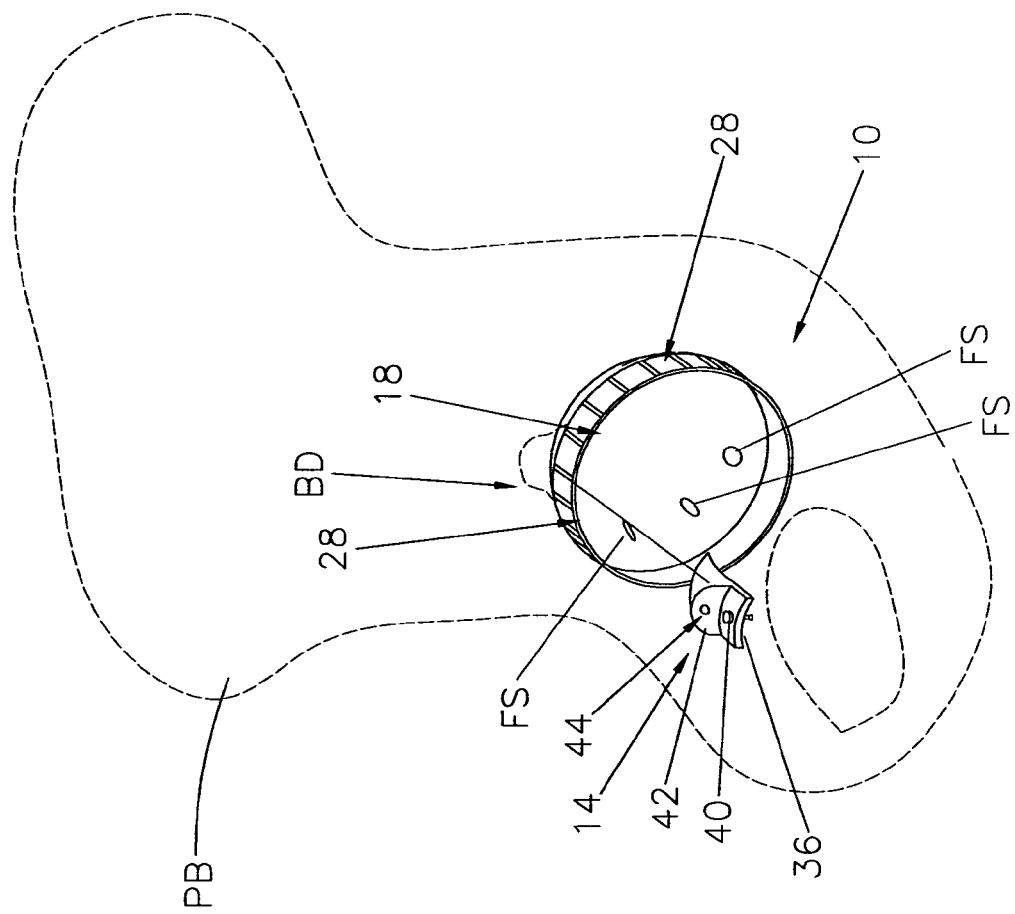
FIG. 11A is a perspective view of the acetabular cup of the present invention impacted and stabilized in the acetabulum cavity with the acetabular augment.

Once the acetabular cup 16 is stabilized within the acetabulum cavity AC, an acetabular augment 14 and augment coupling element 32 are assembled together and aligned with the groove 28 as shown in FIGS. 10 and 11A. The distal portion of the augment coupling element 32 is then placed in the groove 28 and moved along the groove 28 toward the apex 30 of the acetabular cup 16 until the acetabular augment 14 engages the lateral ilia bone. The acetabular augment 14 is then positioned to firmly engage the outer surface of the acetabular cup 16. The acetabular augment 14 is then anchored to the later ilia bone by fasteners 46 and the acetabular augment is secured to the acetabular cup 16 by tightening the augment coupling element 32 as shown in FIGS. 12 and 12A.

As shown in FIG. 10, 11, 11A, 12 and 12A, the bone engaging surface 42 of the acetabular augment 14 may comprise a bulbous or convex arcuate shape at least partially disposed within the bony deficiency BD to further stabilize the acetabular cup 16.

One preferred method of implanting the acetabular cup comprises the steps of:
  preparing the acetabulum to receive the acetabular cup;
  determining the preferred orientation of the acetabular cup relative to the prepared acetabulum site;
  positioning the acetabular cup in the acetabulum in the preferred orientation;
  impacting the acetabular cup into the acetabulum in the preferred orientation;
  stabilizing the impacted acetabular cup in the preferred orientation in the acetabulum;
  assembling the acetabular augment and the augment coupling element together;
  positioning at least a portion of the augment coupling element within the groove of the acetabular cup;
  sliding the acetabular coupling element along the groove toward the apex until the acetabular augment engages the lateral ilia bone;
  positioning the acetabular augment to engage the outer surface of the acetabular cup;
  anchoring the acetabular augment to the lateral ilia bone; and
  securing the acetabular augment to the acetabular cup by tightening the augment coupling element.

Alternately, the acetabular cup 16 and the acetabular augment 14 may be assembly with the augment coupling element 32 before placing the acetabular cup 16 in the acetabulum cavity AC.

There are instances when initial acetabular cup stability cannot be obtained due to severe bony deficiency of the acetabulum. In such cases, a trial acetabular cup and trial acetabular augment may be used to create a model for the assembly of an acetabular cup implant and acetabular augment implant coupled together by an augment coupling element.

One such method comprises the steps of:
  preparing the acetabulum to receive the acetabular cup implant;
  determining the preferred orientation of the acetabular cup implant and acetabular augment implant relative to the prepared acetabulum site;
  positioning the trial acetabular cup in the prepared acetabulum site in the preferred orientation;
  assembling the trial acetabular augment and the trial augment coupling element together;
  positioning at least a portion of the trial augment coupling element within the groove of the trial acetabular cup;
  sliding the trial acetabular coupling element along the groove toward the apex until the trial acetabular augment engages the lateral ilia bone to establish the proper position of the trial acetabular augment within the groove of the trial acetabular cup;

securing the trial acetabular augment to the trial acetabular cup to maintain the trial acetabular augment in the proper position within the groove of the trial acetabular cup by tightening the trial augment coupling element;

removing the assembled trial acetabular cup and trial acetabular augment from the prepared acetabulum site;

assembling the acetabular cup implant and acetabular augment implant into an integrated implant by prepositioning the augment coupling element implant longitudinally in the groove of the acetabular cup implant using the assembled trial acetabular cup and the trial acetabular augment as a model and securing the acetabular augment implant to the acetabular cup implant by tightening the augment coupling element;

positioning the assembled acetabular cup implant and acetabular augment implant in the prepared acetabulum site in the preferred orientation;

impacting the acetabular cup in the preferred orientation in the acetabulum as the acetabular augment implant engages the lateral ilia bone;

stabilizing the impacted acetabular cup implant in the prepared acetabulum site in the preferred orientation; and anchoring the acetabular augment implant to the lateral ilia bone.

Alternately, the trial acetabular cup 16 may be positioned in the acetabulum cavity AC before attaching the acetabular augment 14 and augment coupling element 32.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method of anchoring an acetabular cup having at least one groove formed on the outer surface thereof extending from the base toward the apex thereof to the ilia bone by at least one acetabular augment secured together by a corresponding augment coupling element for a prosthetic hip implant comprising the steps of:

preparing the acetabulum to receive the acetabular cup;

determining the preferred orientation of the acetabular cup relative to the prepared acetabulum site;

positioning the acetabular cup in the acetabulum in the preferred orientation;

impacting the acetabular cup into the acetabulum in the preferred orientation;

stabilizing the impacted acetabular cup in the preferred orientation in the acetabulum;

assembling the acetabular augment and the augment coupling element together;

positioning at least a portion of the augment coupling element within the groove of the acetabular cup;

sliding the acetabular coupling element along the groove toward the apex until the acetabular augment engages the lateral ilia bone;

positioning the acetabular augment to engage the outer surface of the acetabular cup;

anchoring the acetabular augment to the lateral ilia bone; and securing the acetabular augment to the acetabular cup by tightening the augment coupling element.

2. A method of anchoring an acetabular cup having at least one groove formed on the outer surface thereof extending from the base toward the apex thereof to the ilia bone by an acetabular augment secured together by an augment coupling element for a prosthetic hip implant comprising the steps of:

preparing the acetabulum to receive the acetabular cup;

determining the preferred orientation of the assembled acetabular cup and acetabular augment relative to the prepared acetabulum site;

assembling the acetabular cup and the acetabular augment together with the augment coupling element;

positioning at least a portion of the augment coupling element within the groove of the acetabular cup;

positioning the assembled acetabular cup and acetabular augment in the prepared acetabulum site in the preferred orientation;

impacting the acetabular cup in the preferred orientation in the prepared acetabulum site with the acetabular augment loosely fastened to the acetabular cup;

stabilizing the impacted acetabular cup in the preferred orientation;

sliding the acetabular coupling element longitudinally along the groove toward the apex until the acetabular augment engages the lateral ilia bone;

positioning the acetabular augment to engage the outer surface of the acetabular cup;

anchoring the acetabular augment to the lateral ilia bone; and securing the acetabular augment to the acetabular cup by tightening the augment coupling element.

3. A method of anchoring an acetabular cup implant having at least one groove formed on the outer surface thereof extending from the base toward the apex thereof by at least one acetabular augment implant secured together by a corresponding augment coupling element for a prosthetic hip implant using a trial acetabular cup, trial acetubular augment and trial augment coupling element to a model for assembly of the acetabular cup implant and acetabular augment implant comprising the steps of:

preparing the acetabulum to receive the acetabular cup implant;

determining the preferred orientation of the acetabular cup implant and acetabular augment implant relative to the prepared acetabulum site;

positioning the trial acetabular cup in the prepared acetabulum site in the preferred orientation;

assembling the trial acetabular augment and the trial augment coupling element together;

positioning at least a portion of the trial augment coupling element within the groove of the trial acetabular cup;

sliding the trial acetabular coupling element along the groove toward the apex until the trial acetabular augment engages the lateral ilia bone to establish the proper position of the trial acetabular augment within the groove of the trial acetabular cup;

securing the trial acetabular augment to the trial acetabular cup to maintain the trial acetabular augment in the proper position within the groove of the trial acetabular cup by tightening the trial augment coupling element;

removing the assembled trial acetabular cup and trial acetabular augment from the prepared acetabulum site;

assembling the acetabular cup implant and acetabular augment implant into an integrated implant by prepositioning the augment coupling element implant longitudinally in the groove of the acetabular cup implant using the assembled trial acetabular cup and the trial acetabular augment as a model and securing the acetabular augment implant to the acetabular cup implant by tightening the augment coupling element;

positioning the assembled acetabular cup implant and acetabular augment implant in the prepared acetabulum site in the preferred orientation;

impacting the acetabular cup in the preferred orientation in the acetabulum as the acetabular augment implant engages the lateral ilia bone;

stabilizing the impacted acetabular cup implant in the prepared acetabulum site in the preferred orientation; and anchoring the acetabular augment implant to the lateral ilia bone.

4. A method of anchoring an acetabular cup having at least one groove formed on the outer surface thereof extending from the base toward the apex thereof to the ilia bone by an acetabular augment secured together by an augment coupling element for a prosthetic hip implant using a trial acetabular cup and trial acetabular augment as a model comprising the steps of:

preparing the acetabulum to receive the acetabular cup;

determining the preferred orientation of the assembled trial acetabular cup and trial acetabular augment relative to the prepared acetabulum site;

assembling the trial acetabular cup and the trial acetabular augment together with the trial augment coupling element;

positioning at least a portion of the trial augment coupling element with the groove of the trial acetabular cup;

positioning the assembled trial acetabular cup and trial acetabular augment in the prepared acetabulum site in the preferred orientation;

sliding the trial augment coupling element longitudinally within the groove toward the apex until the trial acetabular augment engages the lateral ilia bone to establish the position of the trial acetabular augment with the groove of the trial acetabular cup;

securing the trial acetabular augment to the trial acetabular cup to maintain the trial acetabular augment in the proper position within the selected groove of the trial acetabular cup by tightening the trial augment coupling element;

removing the assembled trial acetabular cup and trial acetabular augment from the prepared acetabulum site;

assembling the acetabular cup implant and acetabular augment implant into an integrated unit by prepositioning the acetabular augment longitudinally in the groove of the acetabular cup implant and securing the acetabular augment implant to the acetabular cup using the trial acetabular cup and the trial acetabular augment as a model;

positioning the assembled acetabular cup implant and acetabular augment implant in the acetabulum in the prepared acetabulum site in the preferred orientation;

impacting the trial acetabular cup in the preferred orientation in the acetabulum with the acetabular augment implant secured thereto;

stabilizing the impacted acetabular cup implant in the preferred orientation; and anchoring the acetabular augment implant to the lateral ilia bone.

5. A method of anchoring an acetabular cup having at least one groove formed on the outer surface thereof extending from the base toward the apex thereof by at least one acetabular augment secured together by a corresponding augment coupling element for a prosthetic hip implant using a trial acetabular cup and trial acetubular augment as a model comprising the steps of:

preparing the acetabulum to receive the acetabular cup;

loosely assembling the trial acetabular augment within the groove of the trial acetabular cup with the augment coupling element;

placing the loosely assembled trial acetabular cup and trial acetabular augment in the prepared acetabulum site;

determining the preferred orientation of the trial acetabular cup and trial acetabular augment relative to the prepared acetabulum site;

positioning the trial acetabular cup and the trial acetabular augment in the prepared acetabulum site in the preferred orientation;

sliding the trial acetabular augment longitudinally along the groove toward the apex to engage the lateral ilia bone to establish the proper position of the trial acetabular augment within the selected groove of the trial acetabular cup;

securing the trial acetabular augment to the trial acetabular cup by the augment coupling element to maintain the trial acetabular augment in the proper position within the groove of the trial acetabular cup;

removing the trial acetabular cup and trial acetabular augment from the prepared acetabulum site;

assembling the acetabular cup and acetabular augment into an integrated unit by prepositioning the acetabular augment longitudinally in the groove of the acetabular cup and securing the acetabular augment to the acetabular cup with the augment coupling element using the trial acetabular cup and the trial acetabular augment as a model;

positioning the acetabular cup and the acetabular augment in the prepared acetabulum site in the preferred orientation;

impacting the acetabular cup in the preferred orientation in the acetabulum as the acetabular augment engages the lateral ilia bone;

stabilizing the impacted acetabular cup in the prepared acetabulum site in the preferred orientation; and anchoring the acetabular augment to the lateral ilia bone.

* * * * *